United States Patent [19] [11] Patent Number: 5,071,656
Lee et al. [45] Date of Patent: Dec. 10, 1991

[54] DELAYED ONSET TRANSDERMAL DELIVERY DEVICE

[75] Inventors: Eun Soo Lee, Redwood City; Felix Theeuwes, Los Altos Hills; Patrick S. L. Wong, Hayward; Su Il Yum, Los Altos; Alejandro Zaffaroni, Atherton, all of Calif.

[73] Assignee: ALZA Corporation, Palo Alto, Calif.

[21] Appl. No.: 271,207

[22] Filed: Nov. 14, 1988

Related U.S. Application Data

[63] Continuation of Ser. No. 22,301, Mar. 5, 1987, abandoned.

[51] Int. Cl.⁵ ............................................. A61F 13/02
[52] U.S. Cl. ................................... 424/448; 424/449; 424/447
[58] Field of Search ................ 424/446, 447, 448, 449

[56] References Cited

U.S. PATENT DOCUMENTS

| 2,381,621 | 8/1945 | Schmelkes et al. | 167/84 |
| 3,598,122 | 8/1971 | Zaffaroni | 128/268 |
| 3,797,494 | 3/1974 | Zaffaroni | 128/268 |
| 3,923,939 | 12/1975 | Baker et al. | 264/49 |
| 3,948,262 | 4/1976 | Zaffaroni | 128/260 |
| 3,972,995 | 8/1976 | Tsuk et al. | 424/28 |
| 4,286,592 | 9/1981 | Chandrasekaran | 128/260 |
| 4,379,454 | 4/1983 | Campbell et al. | 604/897 |
| 4,409,206 | 10/1983 | Stricker | 424/81 |
| 4,568,343 | 2/1986 | Leeper et al. | 604/896 |
| 4,573,995 | 3/1986 | Cheng et al. | 604/896 |
| 4,573,996 | 3/1986 | Kwiatek et al. | 604/896 |
| 4,588,580 | 5/1986 | Gale et al. | 424/21 |
| 4,668,232 | 5/1987 | Cordes et al. | 604/897 |
| 4,696,821 | 9/1987 | Belsole | 424/448 |

FOREIGN PATENT DOCUMENTS

| 0020777 | 1/1981 | European Pat. Off. | |
| 0050480 | 4/1982 | European Pat. Off. | |
| 0086093 | 8/1983 | European Pat. Off. | |
| 0147780 | 7/1985 | European Pat. Off. | |
| 57-4917 | 1/1982 | Japan | |
| 079864 | 1/1982 | Japan | 128/156 |
| 2117239 | 10/1983 | United Kingdom | |

OTHER PUBLICATIONS

W. J. Roff and J. R. Scott, Handbook of Common Polymers, Section 6: Polyvinyl Acetate, pp. 66-71, CRC Press.

Primary Examiner—Thurman K. Page
Assistant Examiner—Leon R. Horne
Attorney, Agent, or Firm—Jacqueline S. Larson; Edward L. Mandell; Steven F. Stone

[57] ABSTRACT

A diffusional drug delivery device is described which can provide for delayed onset of therapeutic effect and for delivery of the therapeutic agent in predetermined temporal patterns at optimum rates. Delay means are provided between the agent reservoir and the surface through which the agent is released by diffusion to delay the release of agent at a therapeutic rate for predetermined times after application. Suitable means include a delay membrane disposed between the releasing surface and the agent reservoir which membrane is preferably free of undissolved agent and/or is initially impermeable to the agent and thereafter becomes permeable. One or more agent chambers defined by one or more of such membranes may be provided, whereby agents are released in a predetermined temporal pattern at optimal release rates. Delayed permeability enables programmed washout periods to be obtained from the sequential and concurrent application of devices for the administration of drugs, such as nitrates, to which patients may develop a tolerance on continuous administration over extended time periods.

26 Claims, 5 Drawing Sheets

DELAYED ONSET TRANSDERMAL DELIVERY DEVICE

CROSS-REFERENCE TO RELATED APPLICATIONS

This application is a continuation of U.S. patent application Ser. No. 07/022,301 filed Mar. 5, 1987 now abandoned, which in turn is a continuation of U.S. patent application Ser. No. 06/874,263 filed June 13, 1986, now abandoned, which applications are assigned to ALZA Corporation and are incorporated herein by reference and benefit is claimed of their filing dates. This application is also related to U.S. patent application Ser. No. 07/271,122, filed Nov. 14, 1988 which is a continuation of U.S. patent application Ser. No. 06/874,263 filed June 13, 1986, now abandoned.

FIELD OF THE INVENTION

The invention relates to diffusional drug delivery devices, and more particularly to such devices which release drugs at predetermined intervals after being placed at the site of administration.

BACKGROUND OF THE INVENTION

Illustrative examples of diffusional drug delivery device are found in U.S. Pat. Nos. 3,598,122 and 3,948,262 to Zaffaroni and 4,379,454 to Campbell et al, which are incorporated herein by reference. In these devices a drug or other active agent is released by diffusion from a reservoir through the agent releasing surface of the device to the biological environment at which the device is applied. Such devices perform well in the administration of many agents but are not suitable for the administration of an agent whose dosage regime requires that the onset of therapeutic effect be delayed for a significant period of time after application of the device at the site of delivery. This is because the surface through which the agent is released, at the time of application, contains the agent in an amount that is significant compared to the amount in the body that gives rise to a therapeutic concentration. In those devices which utilize an agent reservoir which contains an agent at a concentration above the saturation concentration of the agent in the material from which the reservoir is formed, the agent will be present at the agent releasing surface at the saturation concentration of the agent in the material from which the releasing surface is formed. Saturation concentration is equivalent to a thermodynamic activity of 1 (unit activity). When prior art diffusional devices are applied, agent is immediately available for diffusion into the body and the concentration of the agent at the releasing surface rapidly decreases as the concentration gradient required for steady-state diffusional delivery is established by the absorption of the agent from the releasing surface into the body. In some cases the initial rate of release is unacceptably high and a method for reducing this initial "burst" of agent delivery is described in U.S. Pat. No. 3,923,939 to Baker et al. Even in this patent, the agent releasing surface of the diffusional embodiment contains the agent at the saturation concentration of the agent in the material in which it is dispersed and delivery commences immediately in the manner described above.

Non-diffusional devices are known which do not immediately present drug to the biological environment when installed, such as devices which contain material in breakable microcapsules, or the fluid imbibing pump described in commonly assigned U.S. Pat. No. 4,655,766, of Theeuwes, et al, filed Apr. 17, 1986 for Fluid Imbibing Pump With Self-Regulating Skin Patch. Diffusional delivery devices known to the prior art, however, do not possess this capability.

In addition to providing for a delay, there also exists a need to provide for the sequential, patterned delivery of different agents which may be required in multi-drug regimens.

Currently, oral dosage forms are prescribed in an attempt to meet complex administration objectives. This method requires a high degree of patient cooperation and discipline and often results in improper dosage. Insertable, implantable or transdermal diffusional delivery devices provide improved patient compliance and assured dosage but, for numerous reasons, have heretofore not been adaptable to complex administration of varying dosages of like or different drugs at predetermined intervals from a single delivery device.

The devices of this invention are particularly useful in providing a predetermined, delayed onset of therapeutic effect for any desired time period after application to the skin. Thus, a device could be removed and a new one applied simultaneously, wherein the desired drug-free interval is obtained.

An attempt to address the problems associated with combining different agents in one diffusional device is disclosed in U.S. Pat. No. 2,381,621 to Schmelkes which relates to a dressing for a moist lesion containing multiple medications. The medications are dispersed in separate layers of impermeable material prior to use and upon application to the lesion, the dressing rapidly absorbs water, allowing the separate layers to become permeable to the medications and promptly administering them to the lesion. The devices of Schaelkes all begin to deliver medication upon application and result in substantially concurrent, rather than sequential administration of the multiple medications.

One of the advantages of a continuous release dosage form, such as a transdermal drug delivery device, is the improvement in patient compliance that is obtained from the concurrent removal of one device and application of a new device at the same time. This advantage is lost when removal and application occur at different times or where onset of a therapeutic effect is desired at an inconvenient time such as shortly prior to arousal. It is not possible, using concurrent application and removal of diffusional delivery devices of the prior art to substantially delay the onset of transdermal drug delivery from the time of application, such as at bedtime, until shortly prior to arousal. While other, non-diffusional delivery devices exist which can deliver drug after an extended delay, diffusional devices of the prior art do not possess this capability and rapidly commence delivering the drug at their intended therapeutic rates.

It is accordingly an object of this invention to provide a diffusional agent delivery device which provides for delayed onset of agent administration.

It is another object of this invention to provide a diffusional delivery device for delivering multiple agents in a predetermined, sequential pattern of administration.

It is an additional object to provide for the maintenance of drug potency and device efficacy during prolonged storage periods, whereby the device is inactive while stored, and active when applied to the delivery site.

It is another object to provide for the preprogrammed release of a plurality of drugs, wherein the individual drugs are maintained separated.

It is yet another object of the invention to provide a diffusional delivery device which continuously releases therapeutic agent into a biological environment after a period of no drug delivery.

It is another object of this invention to provide a diffusional delivery device having at least one delay membrane which changes state after application to the site of administration to release drug at the desired rate at a predetermined interval after application.

It is another object of this invention to provide a diffusional transdermal delivery device capable of patterned delivery.

SUMMARY OF THE INVENTION

In accomplishing the foregoing and related objectives, the invention provides a diffusional medical device for the delivery of agents, such as drugs or other biologically active agents in a controlled and preprogrammed manner. As used herein, the terms, "drug" and "agent" are used interchangeably and are intended to have their broadest interpretation as any therapeutically active substance which is delivered to a living organisim to produce a desired, usually beneficial, effect. As used herein, the term "transdermal" is used to mean delivery through the skin or mucosa. A diffusional delivery device, in its broadest sense, comprises an agent reservoir from which agent passes by diffusion to the agent releasing surface of the device and from there into the biological environment to which it is applied. In certain embodiments of the invention, one or more delay membranes are disposed between the agent reservoir and the surface through which the agent is released from the device to produce a delayed onset of agent administration at the intended therapeutic rate. The delay membrane is substantially free of undissolved agent and may be formed from a material which in a first state has a low permeability, and in a second state has a high permeability to the agent whose release is being delayed. Typically there will be at least a factor of two, and preferably at least an order of magnitude, difference in the permeability between the first and second states. In certain preferred embodiments liquid triggers the change of state.

Certain embodiments of this invention possess unique characteristics by which they may be readily distinguished from other diffusional delivery devices. As discussed above, when conventional diffusional devices are placed into operation, the concentration of the agent at the agent releasing surface decreases as the agent at the surface is absorbed by the body. According to certain embodiments of our invention, however, the concentration of the agent at the agent releasing surface actually increases after the device is placed into operation. This occurs because the delay membrane functions to maintain the initial concentration of the agent at the releasing surface of the device substantially below the concentration which will exist when the device is operating at its intended steady-state agent delivery rate. It should be noted this characteristic can also be obtained with a delay membrane that does not undergo a change of state. A diffusional delivery device which uses a delay membrane which does not undergo a change of state is disclosed in copending, coassigned patent application of like date herewith of Urquhart, et al, Ser. No. 06/874,262 for Delayed Onset Delivery Device (which is incorporated herein by reference), which device is also within the broad scope of this invention.

Another characteristic by which certain embodiments of our invention may be distinguished from other diffusional delivery devices has to do with the concentration or loading of agent at the agent releasing surface. As noted above, it is desired, in certain embodiments, that, in its first state, the delay membrane be very impermeable to the agent being delayed. Nevertheless, it must be recognized that nothing is absolutely impermeable and even in preferred embodiments there may be small concentrations of the agent at the releasing surface. Typical delay membranes which undergo a change of state exhibit an extremely low solubility and diffusivity for the agent in their first state. As a result, even if the delay membrane has reached equilibrium with the reservoir, and may be at a thermodynamic activity of unity, the actual concentration or loading of the agent at the releasing surface will be too low to be capable of sustaining a therapeutically effective delivery rate. Thus, if the delay membrane is the agent releasing surface of the device, the small amount of agent at the surface will be rapidly absorbed into the body at the time of application and agent will not be available until the membrane changes state and the concentration is allowed to increase as described above.

A similar condition will exist even if there is another layer, such as an adhesive, which has a high solubility for the agent and which is disposed between the delay membrane and the body. If such a device were allowed to sit for a time sufficient to reach equilibrium (when the thermodynamic activity in the reservoir, delay membrane and adhesive are the same), then the concentration of the agent in the adhesive would be substantially higher than in the delay membrane. If, however, the thickness of the adhesive is small, the actual amount of agent available for immediate administration is likewise small. This small amount will be rapidly absorbed as described above and will not be replenished until the delay membrane changes state or otherwise passes agent at the higher, therapeutically effective rates. This condition is addressed according to this invention by keeping the adhesive layer thin, establishing a shelf life for the product which is sufficiently short with respect to the time to reach equilibrium concentration so that the concentration in the adhesive layer is kept low or a combination thereof.

Accordingly, the agent releasing surfaces of certain embodiments of our invention are characterized by being substantially free of agent at the time they are applied to the body. As used herein, the term, "substantially free of agent" means either free of agent or containing an amount of agent insufficient to establish and maintain therapeutically effective agent delivery rates at the time of application to the delivery site.

In accordance with one embodiment of the invention, a device suitable for transdermal administration has a backing layer which is not permeable to the agent to be delivered. Agent is contained in a reservoir contiguous to the backing layer. The agent may be in solution, in combination with other components, in suspension, or in powder form. A delay membrane is disposed contiguous to the agent reservoir. In one state, the membrane is not permeable to the agent, whereby the agent cannot diffuse from the device. In another state, the membrane is permeable to the agent, and will permit diffusion of the agent at the desired rate.

In accordance with a preferred embodiment of the invention, the delay membrane is activated by moisture, such as is readily available from the site of administration such as the cutaneous surface, particularly in occluded regions. The membrane may alternatively be moistened by dipping into a liquid containing vessel immediately prior to application. Water serves as the activating liquid where the membrane is a hydrophilic polymer. Other liquids, such as ethanol, can change the permeability of particular membranes.

Preferred membrane polymers are hydrophilic or semihydrophilic polymers, including polyvinylalcohol, polyvinylpyrrolidone, or hydroxypropylmethyl cellulose. The backing layer and membrane may be heat sealed, where the membrane polymer is fabricated with integral plasticizer. Alternatively, layers are fastened with an adhesive, such as a polyisobutylene copolymer, or silicone based adhesives.

In accordance with another embodiment of the invention, activatible membranes form chambers, which separate components until activated. In one embodiment, incompatible agents are prevented from interacting by a membrane barrier. Alternatively, agents which act upon the agent are stored within a chamber until activation, whereupon the agents are mutually exposed In another embodiment, agents to be released at different times are provided in separate, non-coplanar chambers.

In accordance with yet another aspect of the invention, the hydrophilic membrane is laminated with heat sealable material, such as polyethylene, whereby the backing layer and laminate are heat sealed to enclose an agent reservoir.

In accordance with yet another embodiment of the invention, a device is installed which presents no drug to the biological environment when initially installed, and which delivers drug by diffusion after a delay.

BRIEF DESCRIPTION OF THE DRAWINGS

Other aspects of the invention will become apparent after considering several illustrative embodiments taken in conjunction with the drawings, in which FIGS. 1-7 are cross-sectional views of devices in accordance with the invention wherein:

FIG. 1. illustrates a single agent reservoir and delay membrane;

FIG. 2. is the device of FIG. 1., further including a rate controlling layer and an adhesive layer;

FIG. 3. illustrates a multi-agent device having three delay membranes;

FIG. 4. illustrates a multi-agent device, wherein agents are separated within membrane formed chambers;

FIG. 5. illustrates a non end-sealed device;

FIG. 6. illustrates a two agent, two membrane, non end-sealed device;

FIG. 7. illustrates the device configuration used in deriving the test results illustrated in FIGS. 11, 12, and 13; and FIGS. 8-10 are theoretical plots of release rate vs time for the devices shown; wherein:

FIG. 8. relates to the device of FIG. 3;

FIGS. 9, 9*a* and 9*b* relate to the device of FIG. 4 and illustrate the simultaneous release of the agents. Relates to the device of FIG. 4.; and FIG. 10. relates to the device of FIG. 6.; and where:

FIGS. 11-13 are actual release rate curves for agent released from devices constructed in accordance with FIG. 7., where:

FIG. 11. represents a device having a polyvinylalcohol delay membrane;

FIG. 12. represents a device having a polyvinypyrrolidone delay membrane; and, FIG. 13. represents a device having an hydroxypropylmethylcellulose delay membrane.

DETAILED DESCRIPTION OF THE INVENTION

With reference to the Figures, the devices shown represent, for purposes of illustration, transdermal delivery devices because these are preferred embodiments of this invention. It must be recognized, however, that this invention is applicable to delivery devices generally and in non-transdermal application certain components such as adhesives and backing layers can be omitted. A transdermal delivery device according to this invention may include an impermeable backing member, an agent reservoir, and a delay membrane which in a first state is impermeable to the agent and in a second state is permeable to the agent. The delay membrane may be a glassy polymer which blocks agent diffusion to the skin and which, in the presence of moisture, swells by absorbing water becoming permeable to the agent.

Transdermal device 100, shown in FIG. 1, includes an impermeable backing support layer 102, an agent matrix 104, and a delay membrane 106. When maintained in contact with a wearer's skin by an adhesive overlay or a belt, buckle or elastic band (not shown), for example, membrane 106 undergoes a change of state whereby the permeability of membrane 106 to the agent and the concentration of the agent therein both start to increase.

Backing support layer 102 is not permeable to the agent. Appropriate materials include metalized polyester films, polyethylene or polypropylene. Agent matrix 104 contains the skin permeable drug desired to be delivered, dissolved or dispensed in a carrier therefor. Agent matrix 104 also contains stabilizing agents, thickeners, permeation enhancers or other additives as is known to the art.

Delay membrane 106 is preferably substantially free of undissolved agent and is fabricated from a material which is impermeable to the agent in a first state such as dry or cold, for example, and permeable to the agent in a corresponding second state such as wet or warm. Glassy, hydrophilic polymers which become permeable upon exposure to water are preferred for certain embodiments because sufficient water for causing the change of state is normally available from skin, particularly when it is occluded.

Examples include polyvinylalcohol (PVA), polyacrylamide, hydroxypropylmethyl cellulose (HPMC), hydroxyethylcellulose, hydroxyaethylcellulose, polyacrylic acid, polyvinylpyrrolidone (PVP), and hydroxyethylmethacrylate (HEMA). Albumin, gelatin and cellulose may also be used. Additionally, delay membranes which are activated by non-aqueous agents may be provided. Activation is achieved by immersing the device in the liquid, such as ethanol, water, or phosphate buffered saline, or by providing isolated releasable liquid within the device. Other mechanisms by which the delay membrane can be controllably converted from impermeable to a permeable state are within the scope of this invention.

Device 100A, shown in FIG. 2, has a rate controlling membrane 108 disposed in combination with delay membrane 106. Rate-controlling membrane 108 may control the release rate of agent from the device, the rate of imbibition of the activating fluid into the device, or both. If membrane 108 controls the release rate of agent, either delay membrane 106 or membrane 108 may be positioned in abutting conformity to agent matrix 104. If membrane 108 controls the rate of water imbibition into the device, and thus the time required to cause membrane 106 to change state, it should be positioned as shown. Rate controlling membrane 108 may be fabricated from permeable, semi-permeable or microporous materials which are known to the art to control the rates of agents or fluids into and out of delivery devices.

Figure 2:
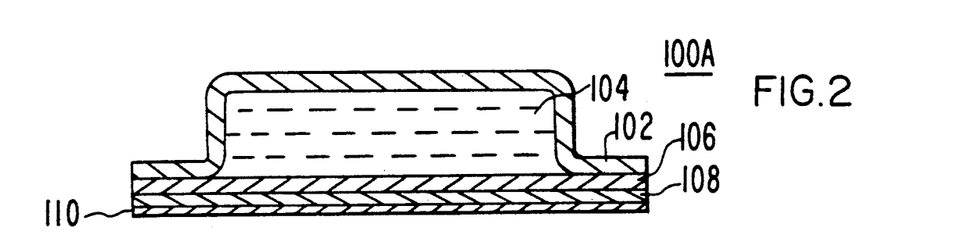

Lamina 110 is an adhesive layer, which, in accordance with one embodiment, contains a predetermined amount of drug which serves to saturate the skin for more rapid therapeutic effects where desired. Silicone compounds are commonly used as adhesives, however numerous materials are known which possess the requisite strength and skin compatibility. An adhesive overlay or other means for maintaining the device on the skin can be employed instead of, or in combination with, adhesive lamina 110.

Figure 3:
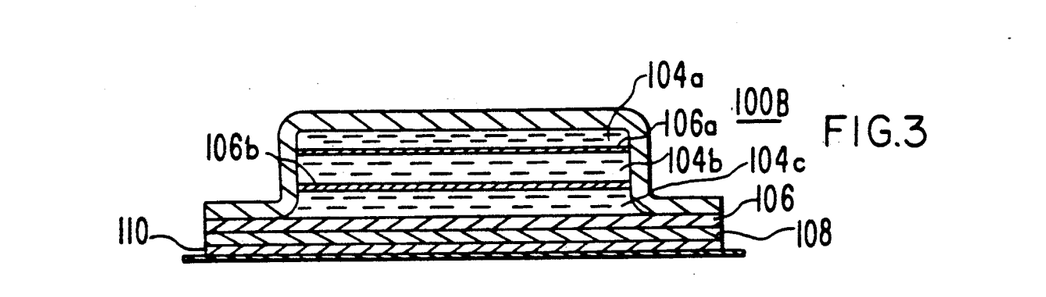

In FIG. 3, an alternative device 100B has a plurality of agent layers 104 a, b and c separated by delay membranes 106 a and b. The agents in layers 104a, b and c may be the same or they may be different or one layer may contain an agent different from that in the other two layers, depending upon the therapeutic regime desired. Membrane 106a prevents mixing of agent in layers 104a and 104b, while membrane 106b separates agent in layers 104b and 104c. The membranes may also have the same or different thickness depending upon the temporal delivery pattern desired and, as shown membrane 106b has a greater thickness than that of membrane 106a. Rate-controlling membrane 108 may control the rate of water imbibition into device 100B so that activation of delay membranes 106a and b can delayed substantially beyond the activation of delay membrane 106 to provide for sequential delivery of the agents in reservoirs.

Figure 1:
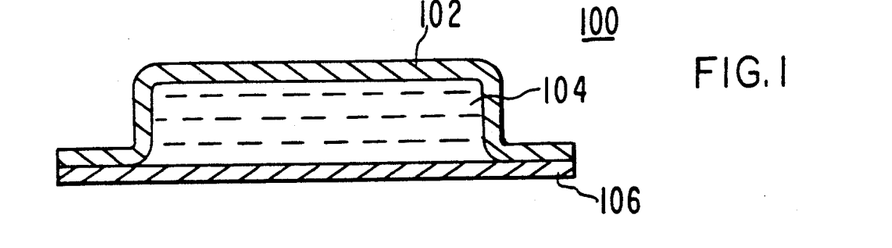

In operation, water migrates into device 100, 100A or 100B, from the skin surface or other source, typically by osmosis or diffusion, passing through intervening layer 110, rate-controlling membrane 108, if any, and then to delay membrane 106. Upon contact with the water, delay membrane 106 becomes progressively more permeable to the agent. Agent in reservoir 104 or 104c diffuses through rate controlling layer 108, and thence through adhesive 110 to the skin surface. As water passes to delay membranes 106b and 106a at a rate established by membrane 108, they, in turn, become more permeable to the agents and the agents are sequentially released from layers 104b and 104a, respectively. As the delivery rates of the agents in each of the reservoirs increase towards their steady-state rates, the concentration of that agent in adhesive 110 also increases. As test results, below, demonstrate, delay membranes require a longer hydration time period as thickness is increased. Accordingly, delay membrane 106a will activate more rapidly than delay membrane 106b if the same material is used in both membranes.

Figure 4:
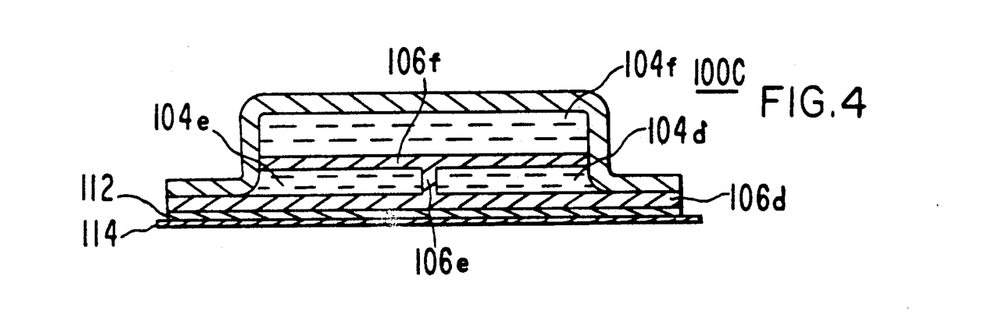

As can be seen in FIG. 4, device 100C has a plurality of agent chambers 104d, e and f, formed by delay membrane 106d, where chambers 104d and 104e are coplanar. A dividing portion 106e separates chambers 104d 104e, and serves to conduct liquid to the portion of delay membrane 106f which underlies agent chamber 104f. Activation of this underlying delay membrane portion can be partially regulated by the thickness of connecting portion 106e. In operation, agent is released from chambers 104d and 104e simultaneously, while agent in chamber 104f is released in substantial quantity at a later time. As shown in FIG. 4, the agents are all maintained separate until the device is activated even though certain agents are released simultaneously. FIG. 4 additionally shows an agent permeable adhesive layer 112 to adhere the device to the skin and a removable release liner 114, typically of siliconized paper.

Figure 5:
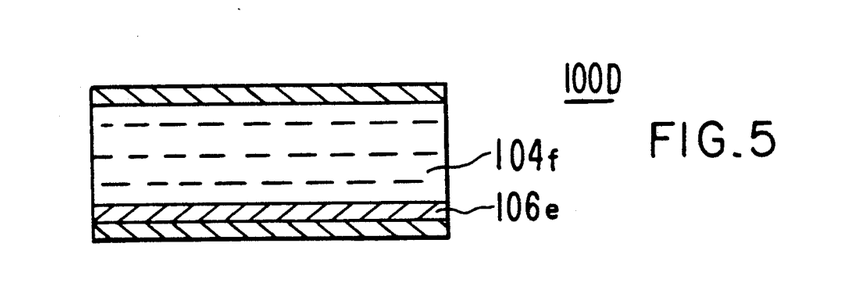
Figure 6:
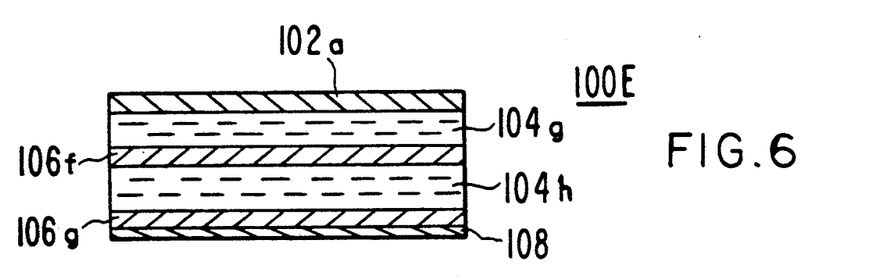

FIGS. 5 and 6 illustrate laminated devices 100D and 100E according to this invention which are not end sealed. Agent reservoir laminae 104 f, g and h may, in addition to permeation enhancers and stabilizing agents, contain rheological modifiers, viscosity boosters or thixotropic/gelling agents to prevent flow of agent matrix beyond the device confines. Delay membranes 106e, f and g do not flow, as these membranes, generally, have a rigid, glass-like rheology when dry. When moistened, or wet, the delay membranes continue to retain integrity.

The device of FIG. 5 is suitable for delaying the onset of therapeutic effect for a period of time after application. The device of FIG. 6 illustrates a configuration which is capable of delivering two agents sequentially or, if the same agent is contained in reservoirs 104g and h, capable of providing a predetermined interruption in administration coupled with a predetermined delay in therapeutic onset. By concurrently applying a fresh device and removing the exhausted device at the same time each day or every other day, for example, a complex repetitive pattern of agent administration can be obtained with a high degree of patient compliance. Thus, if nitroglycerin were the drug delivered in the embodiments of FIGS. 5 & 6, periodic nitroglycerin washout periods would be experienced by the patient which would serve to reduce the development of a tolerance to the drug which may be associated with continuous delivery. In this example the device of FIG. 5 would be a 24 hour device and the device of FIG. 6 would be a 48 hour device. The delay membranes would be selected to produce the desired washout periods, typically considered to be in the range of from 4-12 hours.

Figure 8:
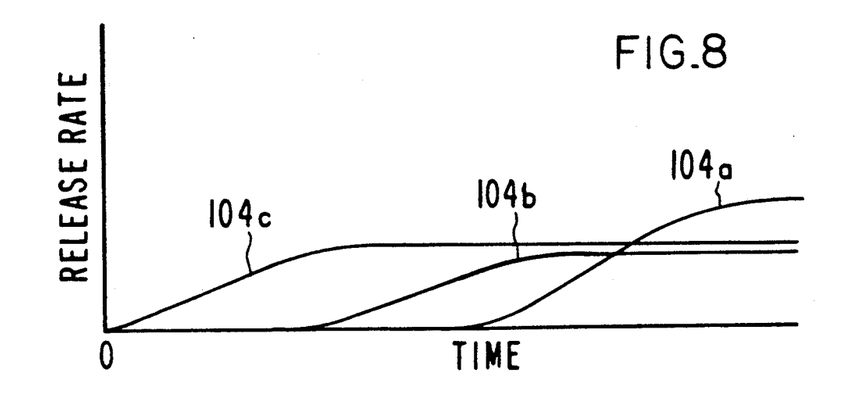
Figure 9A:
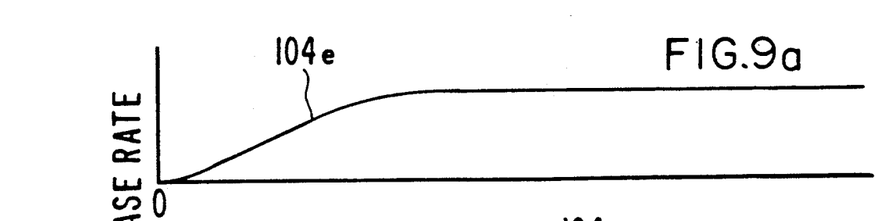
Figure 9B:
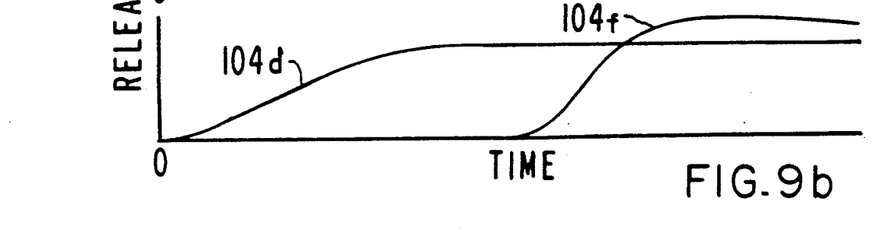
Figure 10:
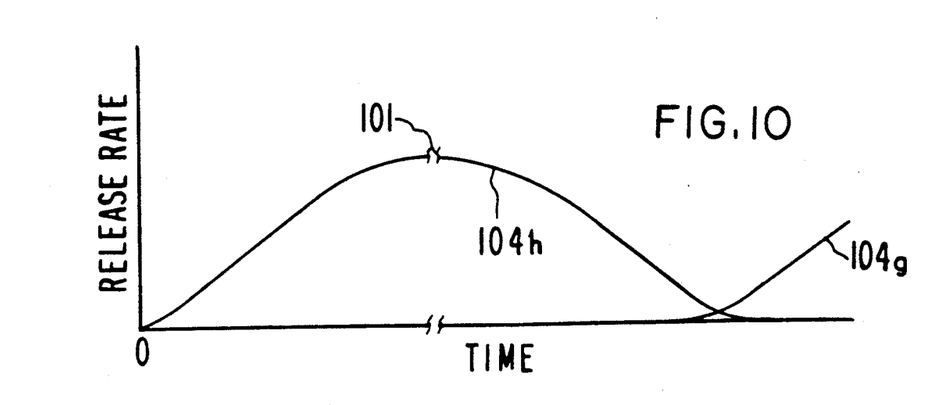

FIGS. 8, 9 and 10 illustrate theoretical release rate vs time curves for the embodiments shown in FIGS. 3, 4 and 6 respectively. In FIG. 8, agent contained in reservoir 104c is released first, with the agents of reservoirs 104b and 104a following sequentially. Rate controlling membrane 108 controls the entry of activation liquid, such as water where hydrophilic delay membranes are used, whereby delay membranes 106, 106b and 106a are sequentially activated.

In FIG. 9, the release pattern of device 100C is illustrated. Separate FIGS. 9a and 9b are provided to clearly illustrate the simultaneous release of agents from matrices 104e and 104d. Agent from matrix 104f is released later, and is maintained at a different release rate.

FIG. 10 illustrates the washout effect produced by device 100E in which membrane 108 controls both the rate of water imbibition into the device and the rate of agent release from the device. The indicated missing time interval 101 represents the substantially constant agent release rate established by membrane 108. Membrane 108 is also selected to control the rate of imbibition of water so that membrane 106f becomes permeable to the agent only after the amount of agent in reservoir 104h has become substantially depleted. This permits the blood levels of the agent to drop in the time period running from the end of period 101 until delivery from reservoir 104g reaches effective rates which occurs when curve 104g continues to rise, in a manner similar to curve 104h.

Having thus generally described our invention, the following specific examples of our invention are provided.

EXAMPLE 1-3

Figure 7:
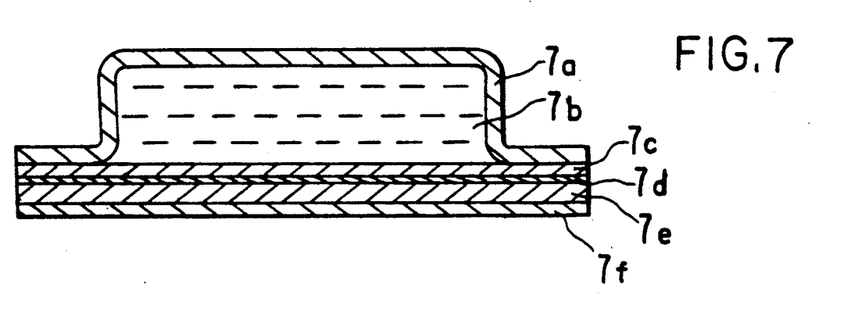

Release rates over time from embodiments of this invention through a 1.5 mil Hytrel membrane, which simulates the water transport properties of human skin, into an aqueous bath at 35° C. were determined for a nitroglycerin delivery device of the type shown in FIG. 7. Backing layer 7a is formed of a composite laminate of retinted polypropylene, polyester, aluminum and ethylene vinyl acetate. Agent reservoir 7b contains 1 part nitroglycerin in 9 parts lactose, 9.3 parts of silicone fluid, and 0.7 parts of colloidal silicon dioxide. Release-rate controlling membrane 7c is 2.0 mils thick, and is composed of ethylene vinylacetate copolymer (EVA) of 9% vinyl acetate, as rate control. Layer 7d is silicone adhesive. Layer 7e is the delay membrane, and is fabricated from polyvinylalcohol (FIG. 11), polyvinylpyrrolidine (FIG.,12), or hydroxypropylmethylcellulose (FIG. 13) at the thicknesses indicated in the graphs in the Figures. Layer 7f is an additional adhesive layer. The control curves in FIGS. 11, 12 and 13 are the theoretical release rates through a 1.5 mil Hytrel film into an aqueous bath at 35° C. of a Transderm-Nitro ® nitroglycerin delivery device available from Ciba-Geigy Corporation which corresponds to the device of FIG. 7 without layers 7e and 7f.

Figure 11:
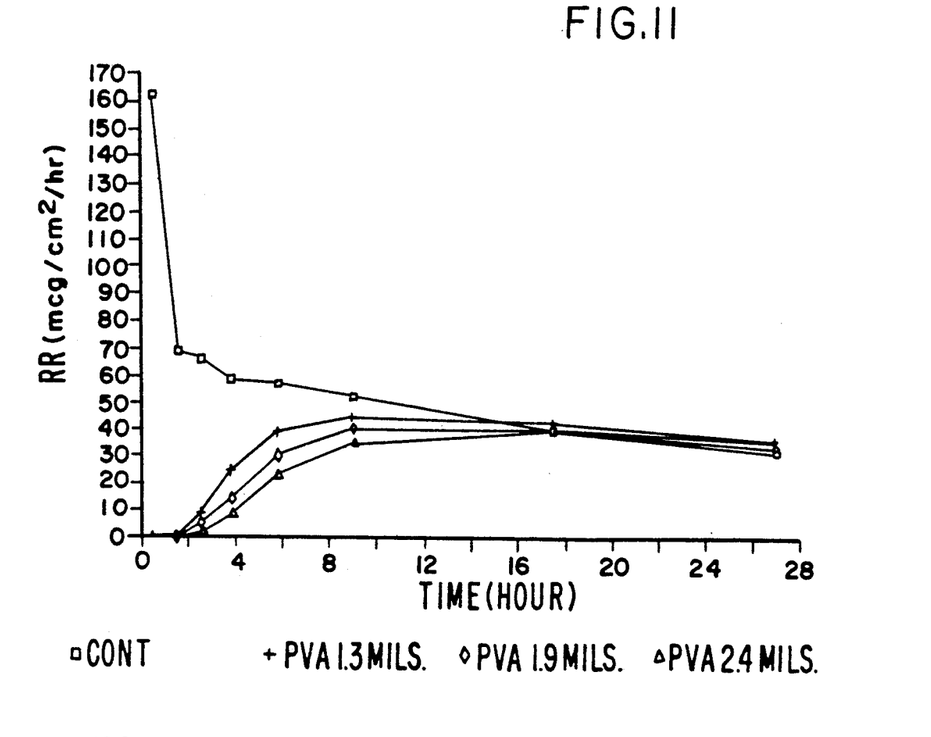
Figure 12:
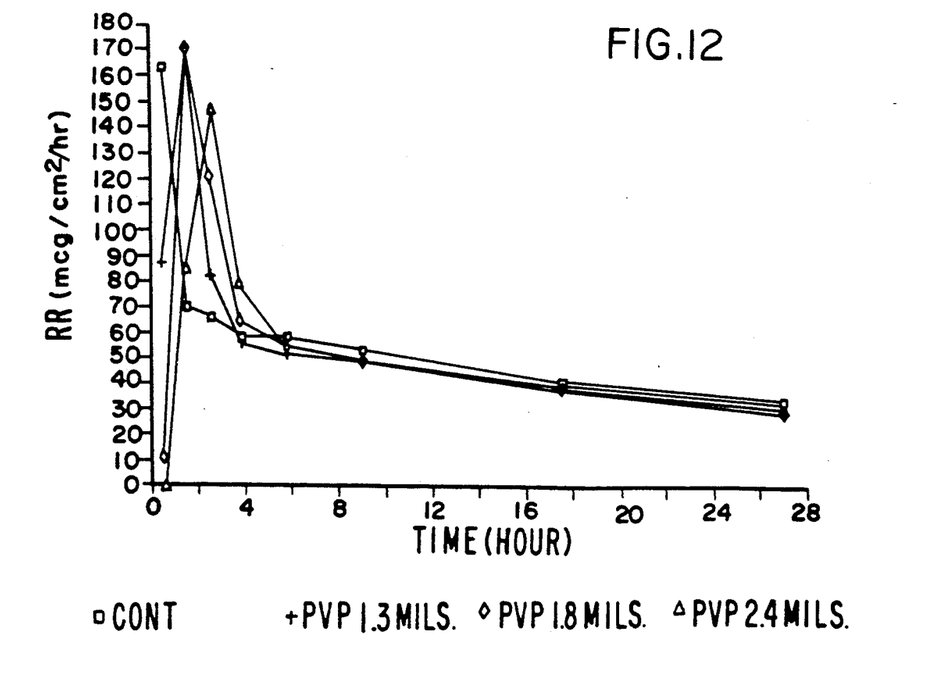
Figure 13:
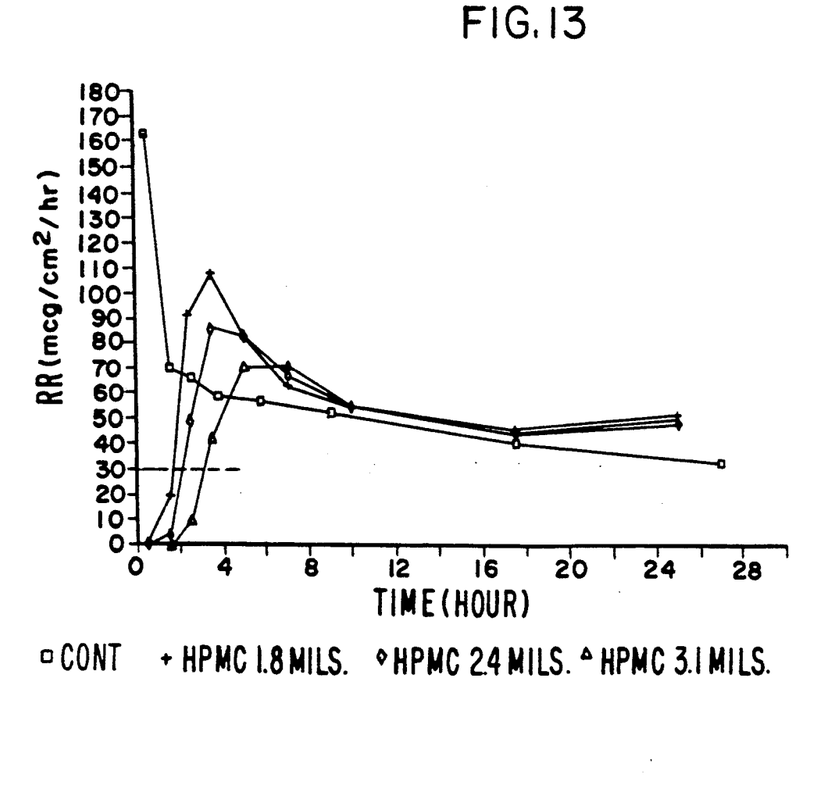

It is clear from FIGS. 11, 12 and 13 that devices incorporating the delay membrane, as compared with the controls, do not immediately release agent when the Hytrel membrane, which simulates the rate at which water would be available to the device from the skin to which it is intended to be applied, is exposed to the aqueous bath. This is due to the fact that Hytrel membrane, which was selected for this test because it is highly permeable to nitroglycerin, imposes substantially no resistance to the diffusion of agent from the test devices to the water and because the agent releasing surfaces 7e of the embodiments of this invention were substantially free of agent when exposed to the bath whereas the corresponding surfaces 7d, of the controls contain nitroglycerin at unit thermodynamic activity.

The Figures show that the delay membranes are capable of in vivo operation as switches, preventing agent release until the device is occluded and provided with sufficient moisture for activation from the skin. The controls will, in vivo immediately present nitroglycerin to the skin and commence nitroglycerin delivery. Devices according to this invention, however, will all exhibit the delays shown before release at the intended steady-state rate will be achieved.

As noted above, during the delay period the concentration of the agent in the agent releasing surface is increasing whereas in the controls it would be decreasing. Polyvinylalcohol demonstrates the longest delay pattern, while polyvinylpyrrolidone demonstrates the shortest for comparable thicknesses of delay membranes. It is also apparent that release characteristics can be adjusted by altering the thickness of the delay membrane. Thick delay membranes cause a longer delay than do thin delay membranes.

Devices according to FIGS. 1, 2, 3, 4, 5, 6 and 7 may be produced by conventional pouching, laminating or extruding techniques as known to the art. The device of FIG. 4, and similarly configured devices which comprise separate, coplanar chambers, may also be produced by modified techniques. In accordance with one method of the invention, drug strips are continuously extruded onto a delay membrane base. Liquid delay membrane is coated over the strips, filling the space between coplanar strips. Additional layers are laminated or extruded over the delay membrane. The product is adhered or heat sealed and cut to shape. Alternatively, discrete blocks of drug matrix may be registered into precut spaces in the delay membrane.

In accordance with the invention, many configurations are constructable, wherein a wide variety of release-rate and delay characteristics are obtainable. Additionally, different agents, or different concentrations of the same agent, are released at predetermined time intervals, whereby highly therapeutic results are obtained with a minimum amount of agent. Moreover, complicated dosage patterns may be administered without dependence on patient compliance, and without interruption in the patient's lifestyle. In accordance with one embodiment, chamber 104d contains the more stable salt form of the agent, and chamber 104e contains a pH modifying agent. As divider 106e becomes permeable, a salt and base mixture is formed to provide for optimal permeability characteristics to the agent. Chambers 104e and 104d are alternatively advantageously employed where the contained agents are chemically incompatible, particularly where degradation of one or both would occur during storage.

In accordance with the above described embodiments, it can additionally be seen how the invention provides for a powerful and flexible means of programming, or coordinating, the diffusional release of one or more agents from a single device, in a single application. Physicians can prescribe a complex agent administration program with far greater assurance that the regime will be adhered to. The patient need not interrupt his/her daily routine to take medication, nor can the patient forget or become confused, with respect to the timing and types of medication which must be taken. Moreover, the amount of agent can be reduced, since therapeutic regimen can be defined more closely with delay membranes, either alone, or in combination with conventional rate controlling membranes. By providing for agent washout, particularly with agents such as nitrates to which patients may develop a tolerance, agent efficacy is enhanced while patient compliance is maintained. Additionally, agents which have limited biological half-lives may be used in lower quantities, now that a means of repeatedly and sequentially reintroducing predetermined amounts of agent has been provided by the invention.

While this invention has been described with respect to certain specific embodiments thereof, it should not be construed as being limited thereto. Numerous modifications and substitutions will suggest themselves to workers skilled in the art and may be made without departing from the scope of this invention which is limited only by the following claims, wherein:

We claim:

1. A controlled release medical device for delivering nitroglycerin to skin or mucosa and adapted to delay the onset of nitroglycerin delivery at a therapeutically effective rate for a predetermined time after placement of said device in nitroglycerin transferring relationship to the skin or mucosa, said device comprising, in combination:
   a nitroglycerin containing reservoir having a surface through which said nitroglycerin is released to the skin or mucosa; and
   a nitroglycerin release delay membrane selected from the group consisting of polyvinyl alcohol, polyvinyl pyrrolidone and hydroxypropylmethylcellulose disposed between the skin or mucosa and the releasing surface of said reservoir, said delay membrane being substantially free of undissolved nitroglycerin and being impermeable to said nitroglycerin in a dry state and permeable thereto in a hydrated state;
   whereby said nitroglycerin must pass through said delay membrane to reach the skin or mucosa and whereby release of said nitroglycerin from said reservoir to the skin or mucosa at said therapeutically effective rate is delayed until the delay membrane is converted from its dry state to its hydrated state.

2. The device of claim 1 wherein said delay membrane is converted from its dry state to its hydrated state by cutaneous liquids.

3. A controlled release medical device for delivering nitroglycerin to the skin or mucosa and adapted to delay the onset of nitroglycerin delivery at a therapeutically effective rate for a predetermined time after placement of said device in nitroglycerin transferring relationship to the skin or mucosa, said device comprising, in combination:
   a first nitroglycerin containing reservoir having a nitroglycerin releasing surface through which said nitroglycerin is released to the skin or mucosa;
   a second nitroglycerin containing reservoir having a nitroglycerin releasing surface through which nitroglycerin from said first and second reservoirs is released to the skin or mucosa; and
   a nitroglycerin release delay membrane selected from the group consisting of polyvinyl alcohol, polyvinyl pyrrolidone and hydroxypropylmethylcellulose disposed between said first and second reservoirs, said delay membrane being substantially free of undissolved nitroglycerin and being impermeable to said nitroglycerin in a dry state and permeable thereto in a hydrated state, said delay membrane being in said dry state when applied to the skin or mucosa;
   whereby delivery of nitroglycerin from said first reservoir will be delayed with respect to delivery of nitroglycerin from said second reservoir until said delay membrane changes to said hydrated state after application to the skin or mucosa and whereby nitroglycerin from said first reservoir must pass through said delay membrane to reach the skin or mucosa.

4. The device of claim 3, further comprising a second delay membrane selected from the group consisting of polyvinyl alcohol, polyvinyl pyrrolidone and hydroxypropylmethylcellulose disposed between the nitroglycerin releasing surface of said second reservoir and the skin or mucosa, whereby delivery of nitroglycerin from said second reservoir will be delayed for a time after said device is placed on the skin or mucosa until said second delay membrane is converted from its dry state to its hydrated state, and whereby delivery of nitroglycerin from said first reservoir will be delayed with respect to delivery of nitroglycerin from said second reservoir until said first and second delay membranes are converted from their dry state to their hydrated state, and whereby nitroglycerin from said first reservoir must pass through said first and second delay membranes and nitroglycerin from said second reservoir must pass through said second delay membrane to reach the skin or mucosa.

5. The device of claim 3 which further comprises a rate controlling means for controlling the rate at which said delay membrane becomes hydrated when placed on the skin or mucosa.

6. The device of claim 4 which further comprises at least one rate controlling means for controlling the rate at which at least one of said delay membranes becomes hydrated when placed on the skin or mucosa.

7. The device of claim 6 wherein a rate controlling means is disposed between said first and second delay membranes.

8. The device of claim 6 wherein a rate controlling means is disposed between said second delay membrane and the skin or mucosa.

9. A medical device for the percutaneous administration of nitroglycerin, said device comprising:
   a backing layer impermeable to nitroglycerin;
   a nitroglycerin reservoir disposed between said backing layer and the skin;
   a nitroglycerin release delay membrane selected from the group consisting of polyvinyl alcohol, polyvinyl pyrrolidone and hydroxypropylmethylcellulose disposed between said reservoir and the skin such that nitroglycerin must pass through said delay membrane to reach the skin, said membrane being substantially free of undissolved nitroglycerin and being impermeable to said nitroglycerin when dry and permeable to said nitroglycerin when hydrated; and
   a means for maintaining said device in nitroglycerin transferring relationship to the skin.

10. The device of claim 9, which further comprises a second nitroglycerin containing reservoir disposed between said backing layer and the skin.

11. The device of claim 10, which further comprises a second nitroglycerin release delay membrane selected from the group consisting of polyvinyl alcohol, polyvinyl pyrrolidone and hydroxypropylmethylcellulose disposed between said second reservoir and the skin.

12. The device of claim 9, which further comprises a rate controlling means for controlling the rate at which said delay membrane becomes hydrated when the device is placed in contact with the skin.

13. The device of claim 11, which further comprises at least one rate controlling means for controlling the rate at which at least one of said delay membranes becomes hydrated when the device is place in contact with the skin.

14. The device of claim 13 wherein a rate controlling means is disposed between said first and second delay membranes.

15. The device of claim 13 wherein a rate controlling means is disposed between said second delay membrane and the skin.

16. A method of delaying delivery of nitroglycerin to the skin or mucosa, said method comprising the steps of:

placing a reservoir of nitroglycerin to be delivered in nitroglycerin transferring relationship to the skin or mucosa;

interposing a substantially nitroglycerin-free nitroglycerin release delay membrane selected from the group consisting of polyvinyl alcohol, polyvinyl pyrrolidone and hydroxypropylmethylcellulose disposed between said reservoir and the skin or mucosa, said delay membrane being impermeable to nitroglycerin in a dry state and permeable thereto in a hydrated state, where said nitroglycerin must pass through said delay membrane to reach the skin or mucosa; and changing said delay membrane from said dry state to said hydrated state after placement at the skin or mucosa; whereby the passage of the nitroglycerin from the reservoir to the skin or mucosa is delayed.

17. The method of claim 16, which further comprises the steps of:

periodically removing said reservoir and delay membrane from the skin or mucosa; and substantially concurrently with said removing step, placing an unused reservoir and delay membrane in nitroglycerin transferring relationship to the skin or mucosa.

18. A medical device for the delivery of nitroglycerin by diffusion from a reservoir thereof to the skin or mucosa, at therapeutically effective rates for a portion of a predetermined application period, the onset of said therapeutic rates commencing a predetermined time after application at the skin or mucosa, said device comprising, in combination:

a reservoir of nitroglycerin; and a nitroglycerin release delay membrane selected from the group consisting of polyvinyl alcohol, polyvinyl pyrrolidone and hydroxypropylmethylcellulose which in a dry state is impermeable to the passage of nitroglycerin and which in a hydrated state is permeable thereto, disposed between said reservoir and the skin or mucosa, said delay membrane having a nitroglycerin releasing surface through which said nitroglycerin is released by diffusion from said reservoir to the skin or mucosa, said delay membrane at the time of application to the skin or mucosa being formed of a material which would be substantially free of said nitroglycerin at thermodynamic equilibrium with said reservoir, and said nitroglycerin releasing surface, at the time of application to the skin or mucosa, containing said nitroglycerin at a concentration substantially lower than the concentration of said nitroglycerin at the onset of said therapeutic rates.

19. The device of claim 18, which further comprises:

a contact adhesive disposed on said nitroglycerin releasing surface.

20. The device of claim 19 wherein the concentration of nitroglycerin in said contact adhesive is greater than the concentration of nitroglycerin in said delay membrane at the time of application, and the total loading of nitroglycerin in said contact adhesive is insufficient to establish and maintain nitroglycerin delivery at a therapeutic rate.

21. A diffusional nitroglycerin delivery device comprising:

a nitroglycerin reservoir; and a diffusion membrane selected from the group consisting of polyvinyl alcohol, polyvinyl pyrrolidone and hydroxypropylmethylcellulose which in a dry state is impermeable to the passage of nitroglycerin and which in a hydrated state is permeable thereto, said diffusion membrane having a nitroglycerin releasing surface through which nitroglycerin is released to the skin or mucosa by diffusion from said reservoir, said nitroglycerin releasing surface being characterized by being substantially free of nitroglycerin when at thermodynamic equilibrium with said reservoir.

22. The device of claim 21 being further characterized by an increase in concentration of said nitroglycerin at said nitroglycerin releasing surface after application of said device to the skin or mucosa.

23. A medical device for the percutaneous administration of nitroglycerin, said device comprising:

a backing layer impermeable to nitroglycerin;

a nitroglycerin reservoir disposed between said backing layer and the skin;

a nitroglycerin release delay membrane selected from the group consisting of polyvinyl alcohol, polyvinyl pyrrolidone and hydroxypropylmethylcellulose disposed between said reservoir and the skin, said delay membrane being impermeable to nitroglycerin when dry and permeable to nitroglycerin when hydrated;

a rate controlling means disposed between said nitroglycerin reservoir and said delay membrane, for controlling the rate at which said delay membrane becomes hydrated when said device is placed in contact with the skin;

an adhesive tie layer interposed between said delay membrane and said reservoir; and a means for maintaining said device in nitroglycerin transferring relationship to the skin.

24. The device of claim 1, 3, 4, 9, 11, 18 or 23 wherein said delay membrane is comprised of polyvinyl alcohol.

25. The method of claim 16 wherein said delay membrane is comprised of polyvinyl alcohol.

26. The device of claim 21 wherein said diffusion membrane is comprised of polyvinyl alcohol.

* * * * *